(12) United States Patent
Hill et al.

(10) Patent No.: US 9,267,139 B2
(45) Date of Patent: Feb. 23, 2016

(54) COMPOSITIONS AND METHODS FOR TREATING MUSCULOSKELETAL DISEASES AND DISORDERS

(71) Applicant: Georgia Regents Research Institute, Inc., Augusta, GA (US)

(72) Inventors: William D. Hill, Augusta, GA (US); Samuel Herberg, Augusta, GA (US); Sudharsan Periyasamy-Thandavan, Martinez, GA (US)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 14/052,390

(22) Filed: Oct. 11, 2013

(65) Prior Publication Data

US 2014/0105869 A1    Apr. 17, 2014

Related U.S. Application Data

(63) Continuation of application No. 61/712,708, filed on Oct. 11, 2012.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 35/28* | (2015.01) |
| *A61K 31/713* | (2006.01) |

(52) U.S. Cl.
CPC .......... *C12N 15/1136* (2013.01); *A61K 31/713* (2013.01); *A61K 35/28* (2013.01); *C12N 15/113* (2013.01); *C12N 2310/113* (2013.01); *C12N 2310/141* (2013.01)

(58) Field of Classification Search
CPC ... C12N 2310/11; C12N 15/113; A16K 48/00
See application file for complete search history.

(56) References Cited

FOREIGN PATENT DOCUMENTS

WO    2009043353    4/2009

OTHER PUBLICATIONS

Cia, et al., "Principles of microRNA regulation of a human cellular signaling network", Mol. Syst. Biol., 2:46 (2006).
Kim, "MicroRNA biogenesis: coordinated cropping and dicing",Nat Rev Mol Cell Biol., 6(5):376-85 (2005).
Aguilar-Pérez, et al., "Alternative Splice Variants of the Osteogenic Cytokine SDF-1 Differentially Mediate CXCR4 and CXCR7 Expression in Bone Marrow MSCs", American Society of Bone and Mineral Research (ASBMR), Houston, Texas, Sep. 12-15, 2014.
Backes, et al., "A dictionary on microRNSs and their putative target pathways", Nucleic Acis Res., 38(13):4476-86 (2010).
Cray, "Nano-drop Printing of SDF-1[2] on DermaMatrix Augments BMP-2-induced Repair of Critical Size Mouse Calvarial Defects", Tissue Engineering and Regenerative Medicine International Society (TERMIS), Washington, D.C, Dec. 13-16, 2014.
Hamrick, et al.,., "Age-related loss of muscle mass and bone strength in mice is associated with a decline in physical activity and serum leptin", Bone 39:845-53 (2006).
Herberg, et al., "Stromal cell-derived factor-1[2] mediates cell survival through enhancing autophagy in bone marrow-derived mesenchymal stem cells", PLoS One,8(3):e58207 (2013a).
Herberg, et al., "Stromal cell-derived factor-1[2] potentiates bone morphogenetic protein-2 stimulated osteoinduction of genetically engineered bone marrow-derived mesenchymal stem cells in vitro", Tissue Eng., 19(1-2):1-13 (2013b).
Herberg, et al., "Low-dose bone morphogenetic protein-2/stromal cell-derived factor-1[2] cotherapy induces bone regeneration in critical-size rat calvarial defects", Tissue Eng Part A. May;20(9-10):1444-53 (2014a).
Herbert, et al., "Total body irradiation is permissive for mesenchymal stem cell-mediated new bone formation following local transplantation", Tissue Engineering part A, 20 (23-24):3212-27 (2014b).
Herberg, et al., "Inkjet-based biopatterning of SDF-1[2] augments BMP-2-induced repair of critical size calvarial bone defects in mice", Bone. 67:95-103 (2014c).
Herberg, et al., "Mesenchymal stem cell expression of stromal cell-derived factor-1[2] augments bone formation in a model of local regenerative therapy", J Orthop Res., 33:174-184 (2015a).
Herberg, et al., "Mesenchymal stem Cell Expression of SDF-1[2] Synergizes with BMP-2 to Augment Cell-Mediated Healing of Critical-Size Mouse Calvarial Defects", Tissue Engineering and Regenerative Medicine, J Tissue Eng Regen Med., (2015).
Herberg, et al., "Bone Marrow-Derived Mesenchymal Stem Cells Conditionally Overexpressing Stromal Cell-Derived Factor-1[2] Development of a Novel Murine Stem Cell Life", International Society of Stem Cell Research (ISSCR) Meeting SanFrancisco, CA Jun. 16-19, 2010a.
Herberg, et al., "Mesenchymal Stem Cells Conditionally Overexpressing Stromal Cell-Derived Factor-1?. Development and Characterization of a Transgenic Mouse Stem Cell Line in vitro", Georgia Life Sciences Summit, Atlanta GA, Oct. 2010b.
Herberg, et al., "SDF-1[2] Over-Expressing BMSCs relative to Empty Vector BMSCs Enhance Healing of Critical-Size Mouse Calvarial Defects in a BMP-2 Co-Therapy model", Tissue Eiingineering and Regenerative Medicine International Society (TERMIS), Washington, D.C, Dec. 13-16, 2014d.
Herberg, et al., "Inkjet-based biopatterning of SDF-1[2] augments BMP-2-Induced repair of critical size mouse calvarial defects", American Society of Bone and Mineral Research (ASBMR), Houston, Texas, Sep. 12-15, 2014e.
Herberg, et al., "SDF-1[2] BMP-2 Co-Therapy Augments BMSC-Mediated Healing of Critical-Size Mouse Calvarial Defects", American Society of Bone and Mineral Research (ASBMR), Houston, Texas, Sep. 12-15, 2014f.

(Continued)

*Primary Examiner* — Amy Bowman
(74) *Attorney, Agent, or Firm* — Pabst Patent Group LLP

(57) ABSTRACT

Compositions and methods for modulating miRNAs up-regulated or down-regulated in aged individuals and their downstream targets are disclosed. Methods of treating musculoskeletal disorders are also provided.

17 Claims, 7 Drawing Sheets

(56) References Cited

OTHER PUBLICATIONS

Herberg, et al., "Suboptimal Bone Morphogenetic Protein-2 / Stromal Cell-Derived Factor-1? Co-Therapy Induces Bone in Critical- Size Rat Calvarial Defects", Tissue Engineering and Regenerative Medicine International Society (TERMIS) 2013 International Conference and Exposition, Atlanta GA, Nov. 10-13, 2013c.
Herberg, et al., "Total-Body Irradiation promotes Engraftment and New Bone Formation upon Local Injection of Mesenchymal Stem Cells in a Murine Tibial Transplant Model", 17th Annual Hilton Head: Regenerative Medicine Workshop, Hilton Head, S.C., Mar. 20-23, 2013d.
Herberg, et al., "SDF-1 is Critical for Bone Regeneration: SDF-$1^2$ Promotes BMP-2 Function", American Society of Bone and Mineral Research (ASBMR), Baltimore, MD, Oct. 3-6, 2013e.
Herberg, et al., "Stromal Cell-derived factor-$1^2$ mediates Bone Morphogenetic Protein Receptor Signaling, Chemotaxis, and Apoptosis-Resistance via Enhancing Autophagy in Murine Mesenchymal Stem Cells in vitro", 17th Annual Hilton Head: Regenerative Medicine Workshop, Hilton Head, S C., Mar. 20-23, 2013f.
Herberg, et al., "Total-Body Irradiation promotes Engraftment and New Bone Formation upon Local Injection of Mesenchymal Stem Cells in a Murine Tibial Transplant Model", 17th Annual Hilton Head: Regenerative Medicine Workshop, Hilton Head, S. C., Mar. 20-23, 2013g.
Herberg, et al., "Stromal Cell-derived factor-$1^2$ mediates Bone Morphogenetic Protein Receptor Signaling, Chemotaxis, and Apoptosis-Resistance via Enhancing Autophagy in Murine Mesenchymal Stem Cells in vitro", American Society of Bone and Mineral Research (ASBMR), Minneapolis, MN, Oct. 12-15, 2012a.
Herberg, et al., "Total- Body Irradiation promotes Engraftment and New Bone Formation upon Local Injection of Mesenchymal Stem Cells in a Murine Tibial Transplant Model" , American Society of Bone and Mineral Research (ASBMR), Minneapolis, MN, Oct. 12-15, 2012b.
Herberg, et al., "Transgenic Adult Murine Mesenchymal Stem Cells Conditionally Overexpressing SDF-$1^2$ Enhance New Bone Formation in Both in Vitro and In Vivo Model Systems" , American Society of Bone and Mineral Research (ASBMR), San Diego CA, Sep. 16-20, 2011a.
Herberg, et al., "Transgenic Adult Murine Mesenchymal Stem Cells Conditionally Overexpressing SDF-$1^2$ Enhance New Bone Formation in Both in Vitro and In Vivo Model Systems" , International Society of Stem Cell Research (ISSCR) Meeting Toronto, Ontario, CA. Jun. 15-18, 2011b.
Hill, "Transgenic Adult Murine Mesenchymal Stem Cells Enhance In Vitro and In Vivo Bone Formation" , 15th Annual Hilton Head: Regenerativie Medicine Workshop, Hilton Head, S.C., Mar. 16-19, 2011.
Hill, "Mesenchymal Stem Cells Conditionally Overexpressing SDF-$1^2$ Drive New Bone Formation" , 16th Annual Hilton Head. Regenerative Medicine Workshop, Hilton Head, S C., Mar. 14-17, 2012.
Hill, "Bad to the Bone:Age-related Changes in Mesenchymal Stem Cell miRNAs and Their Effect on the CXCL12 (SDF-1) Axis and Osteogenesis" , MCG department of Cellular Biology & Anatomy Seminar, Apr. 29, 2014.
Hill, et al., "Curriculum Vitae" , Sep. 15, 2015.
Hill, Project 3, grant submitted May 5, 2015b.
Hill, "Epigenetic based changes in mesenchymal stem cell (MSC) function with aging", Departments of Cellular Biology & Anatomy, UCC Cell Signaling, pp. 1-36, Apr. 10, 2015c.
Liu, et al., "microRNA-29b: an emerging player in human cancer", Asian Pacific J Cancer Prevention, 15:9059-64 (2014).
Molinuevo, et al., "Effect of metformin on bone morrow progenitor cell differentiation: in vivo and in vitro studies", J bone Miner Res., 25(2):211-21 (2010).
Periyasamy-Thandavan, et al., "Differential Expression of MicroRNAs in Human Mesenchymal Stem Cells with Age May Be Related to Musculoskeletal Disorders", American Society of Bone and Mineral Research (ASBMR), Baltimore, MD, Oct. 3-6, 2013a.
Periyasamy-Thandavan, et al., "Age-associated Changes in Osteogenic-linked miRNAs in human mesenchymal stem cells", 17th Annual Hilton Head Regenative Medicine Workshop, Hilton Head S.C., Mar. 20-23, 2013b.
Periyasamy-Thandavan, et al., "Age-associated Changes in MicroRNA Expression Affects Differentiation Potential in Human Mesenchymal Stem Cells", American Society of Bone and Mineral Research (ASBMR), Baltimore, MD, Oct. 3-6, 2013c.
Periyasamy-Thandavan, et al., "Differential Expression of MicroRNAs in Human Mesenchymal Stem Cells with Age May Be Related to Musculoskeletal Disorders", Tissue Engineering and Regenerative Medicine International Society (TERMIS) 2013 International Conference and Exposition, Atlanta GA, Nov. 10-13, 2013d.
Periyasamy-Thandavan, et al., "Differentially Expressing MicroRNAs Negatively Regulates Osteogenic Differentiation in Human Bone Marrow Derived Mesenchymal Stem Cells", 18th Annual Hilton Head. Regenerative Medicine Workshop, Hilton Head, S.C., Mar. 26-29, 2014a.
Periyasamy-Thandavan, et al., "The Age-Associated Rise in miRNAs from Muscle Target SDF-1 and Musculoskeletal regulatory genes is Reversed with Caloric Restriction and Leptin", American Society of Bone and Mineral Research (ASBMR), Houston, Texas, Sep. 12-15, 2014b.
Xu, et al., "Effect of miR-29b-1* and miR-29c knockdown on cell growth of the bladder cancer cell line T24" , J Intl Med Res., 41(6):1803-10 (2013).
Zafari, et al., "Regulatory MicroRNA networks: complex patterns of target pathways for disease-related and housekeeping MicroRNAs", Genomics Proteomics Bioinformatics, 13:159-68 (2015).
Zhang, et al., "Age-related changes in the osteogenic differentiation potential of mouse bone marrow stromal cells", J Bone Mineral Res., 23(7)1118-28 (2008).

COMPOSITIONS AND METHODS FOR TREATING MUSCULOSKELETAL DISEASES AND DISORDERS

CROSS-REFERENCE TO RELATED APPLICATIONS

This application claims the benefit of and priority to U.S. Provisional Application No. 61/712,708, filed on Oct. 11, 2012. The entire disclosure of the above application is incorporated herein by reference.

STATEMENT REGARDING FEDERALLY SPONSORED RESEARCH OR DEVELOPMENT

This invention was made with Government Support under Agreement NIH 1P01AG036675-01A1 awarded by the National Institutes of Health. The Government has certain rights in the invention.

FIELD OF THE INVENTION

The invention is generally related to the field of compositions and methods for the treatment of musculoskeletal diseases and disorders.

BACKGROUND OF THE INVENTION

Osteoporosis and obesity are major public health concerns. Recent estimates indicate that the US population consists of 25% obese, and, among the elderly, 50% of all osteoporotic individuals have age-associated osteoporosis, one of the most common and debilitating types of bone disease. Although the mechanisms involved remain poorly defined, recent studies suggest that age-associated osteoporosis is a stem cell disease. Human bone marrow mesenchymal stromal/stem cells (BMSCs) are multipotent stem cells that can differentiate into osteoblasts. MicroRNAs (miRNAs), a class of short single-stranded noncoding RNAs are post-transcriptional regulators that can modulate the homeostasis of multiple genes and associated pathways simultaneously. Changes in miRNA expression have been linked to the development of numerous disorders, including musculoskeletal disorders. While miRNAs are emerging as important modulators of cell function and phenotype development there remains a need to determine the role of miRNA and their downstream targets in human BMSCs differentiation or in the regulation of bone metabolism with aging.

Accordingly, it is an object of the invention to provide compositions and methods for altering the expression of miRNAs and downstream targets of miRNAs that are important for regulation of BMSC differentiation.

It is another object of the invention to provide compositions and methods for treating musculoskeletal disorders in a subject.

SUMMARY OF THE INVENTION

A genome-wide assessment of miRNA expression led to the discovery that the expression of multiple miRNAs are altered with age. It has also been discovered that the differential miRNA expression in BMSCs with age can regulate age-associated changes that reduce osteogenic capacity and increase the adipogenic fate of these stem cells, and may help drive the development of osteoporosis. Compositions and methods for targeting these miRNAs and their downstream targets, and their use in methods of treating musculoskeletal disorders are provided.

Six miRNAs (miR-579,-1244,-374ab,-671-5p,-370,-29abcd) are significantly up-regulated in aged BMSCs. Predicted bone homeostasis targets of these miRNAs include SDF-1, BMP2, β arrestin, SOX4, Leptin, IGF-1, VEGF, Collagen type 1 α1 and α2. Compositions and methods for modulating expression are of miRNA's miR-579,-1244,-374ab,-671-5p,-370,-29abcd are disclosed. Compositions and methods for modulating downstream targets of miR-579,-1244,-374ab,-671-5p,-370, -29abcd, and combinations thereof are also disclosed. In some embodiments, the downstream targets are SDF-1, BMP2, β arrestin, SOX4, Leptin, IGF-1, VEGF, Collagen type 1 α1 and α2, or a combination thereof.

Eleven miRNAs including miR-1231,-517-ac,-3180-5p were significantly reduced in aged hBMSCs. Predicted targets of these miRNAs included adipogenic genes such as PPAR-gamma or -alpha, AP2-alpha, and CD36. Compositions and methods for modulating expression of the eleven miRNA, including miR-1231,-517-ac,-3180-5p, and combinations thereof are disclosed. Compositions and methods for modulating downstream targets of miR-1231,-517-ac,-3180-5p are also disclosed. In some embodiments, the downstream targets are PPAR-gamma or -alpha, AP2-alpha, CD36, or a combination thereof.

DETAILED DESCRIPTION OF THE INVENTION

I. Definitions

Figure 1A:
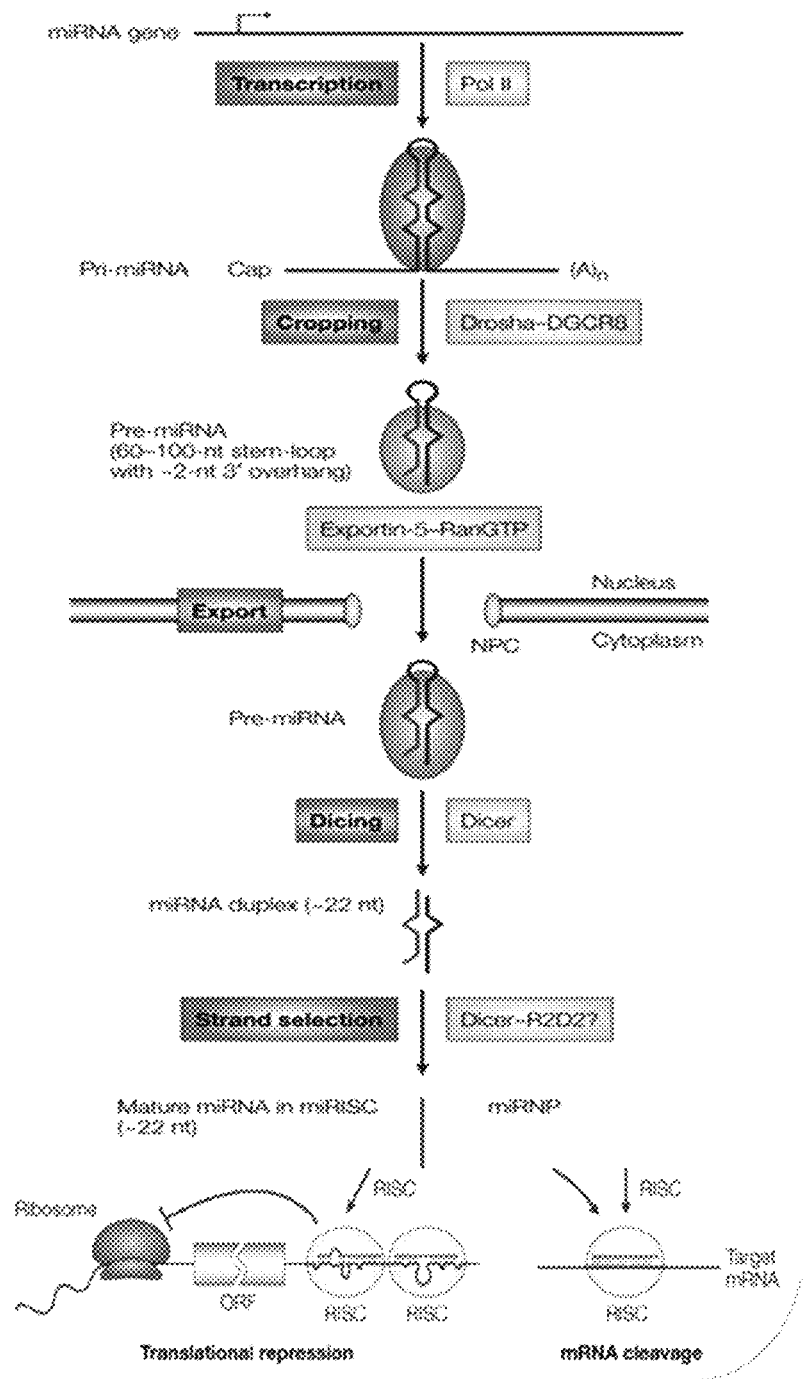
FIG. 1A is a model for microRNA biogenesis. MicroRNA (miRNA) genes are transcribed by RNA polymerase II (pol II) to generate the primary transcripts (pri-miRNAs). The initiation step ('cropping') is mediated by the Drosha-DGCR8 complex. Drosha and DGCR8 are both located mainly in the nucleus. The product of this nuclear processing step is a ~70-nucleotide (nt) pre-miRNA, which possesses a short stem plus a ~2-nucleotide 3' overhang. This structure might serve as a signature motif that is recognized by the nuclear export factor exportin-5. Pre-miRNA constitutes a transport complex together with exportin-5 and its cofactor Ran (the GTP-bound form). Following export, the cytoplasmic RNase III Dicer participates in the second processing step ('dicing') to produce miRNA duplexes. The duplex is separated and usually one strand is selected as the mature miRNA, whereas the other strand is degraded. Reproduced from *Nat Rev Mol Cell Biol.* 2005; 6(5):376-85.
Figure 1B:
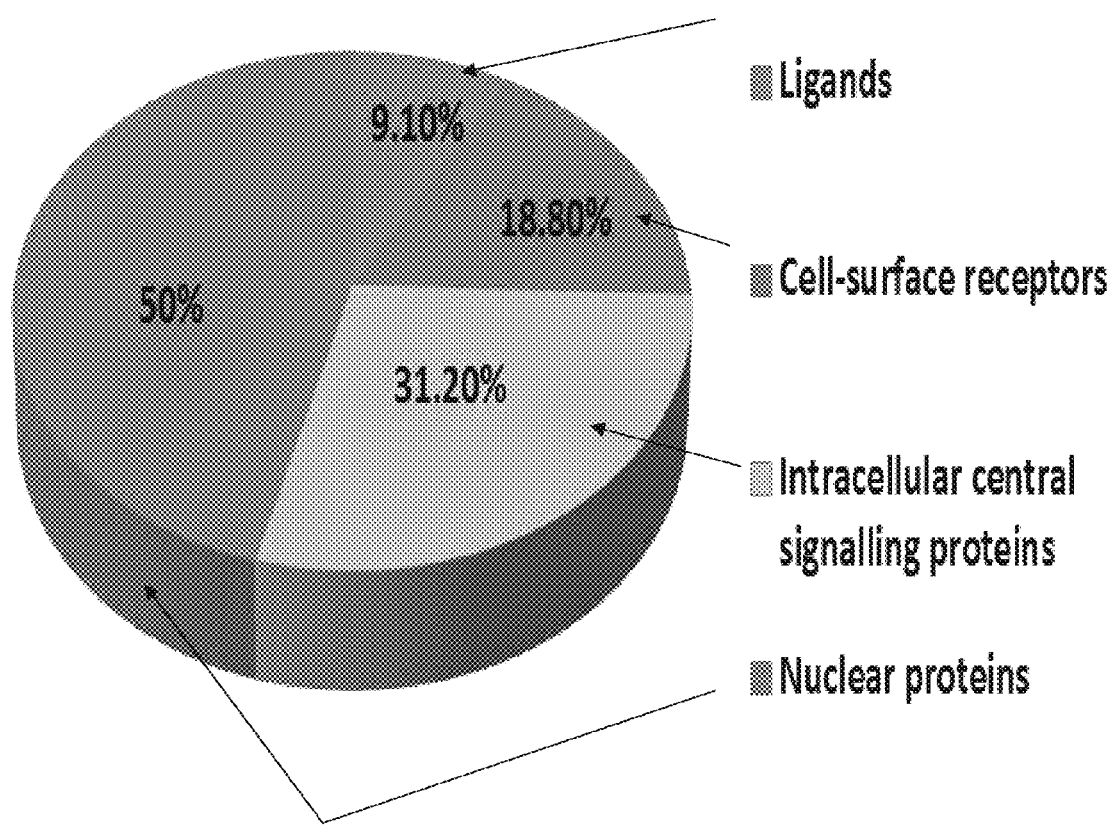
FIG. 1B is a pie chart showing Distribution of miRNA targets in the signal network at different signaling stages.
Figure 1C:
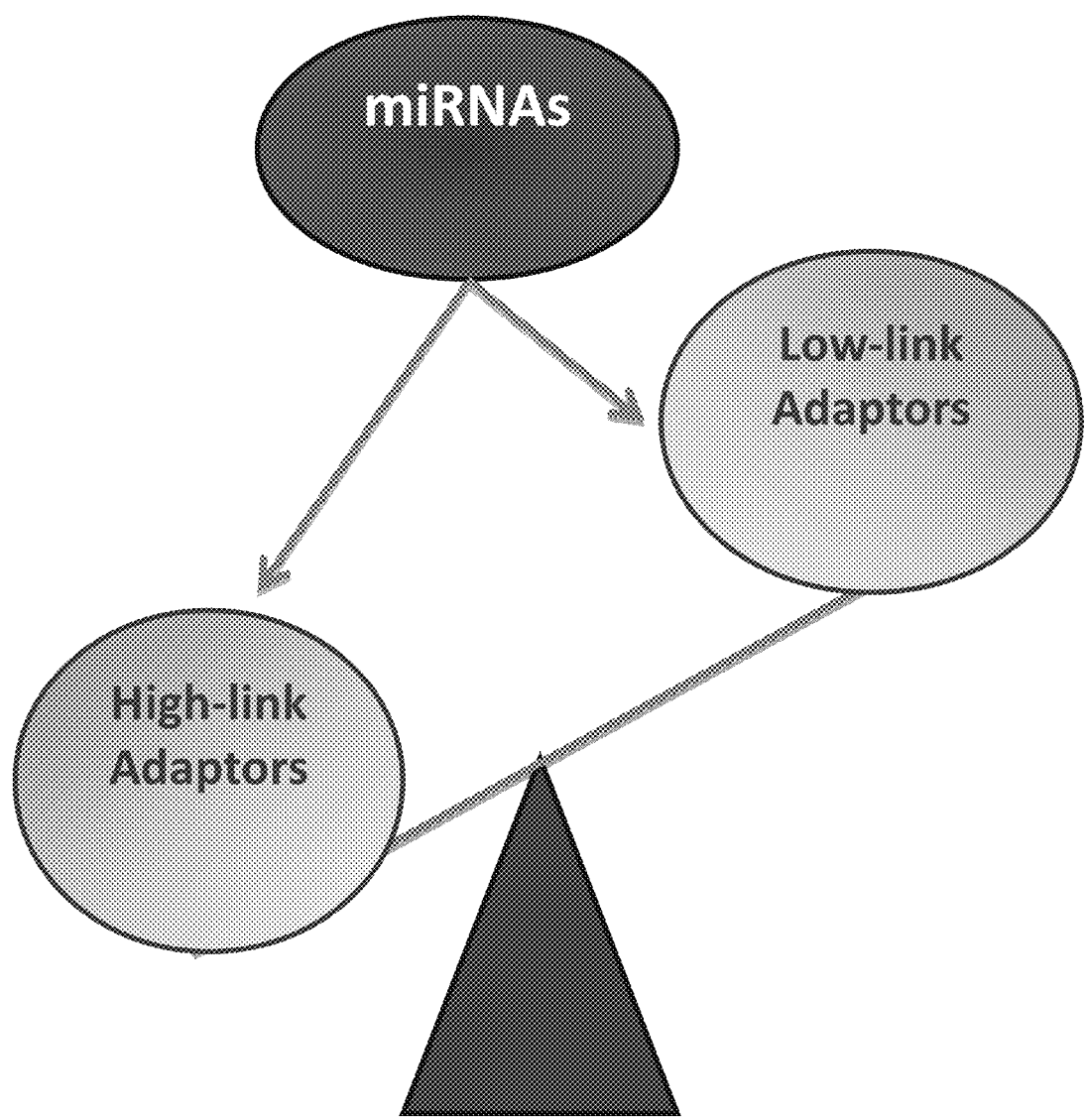
FIG. 1C is a diagram showing miRNAs preferentially target the downstream components of high-link adaptors. Reproduced from *Mol. Syst. Biol.* 2006; 2:46.
Figure 2:
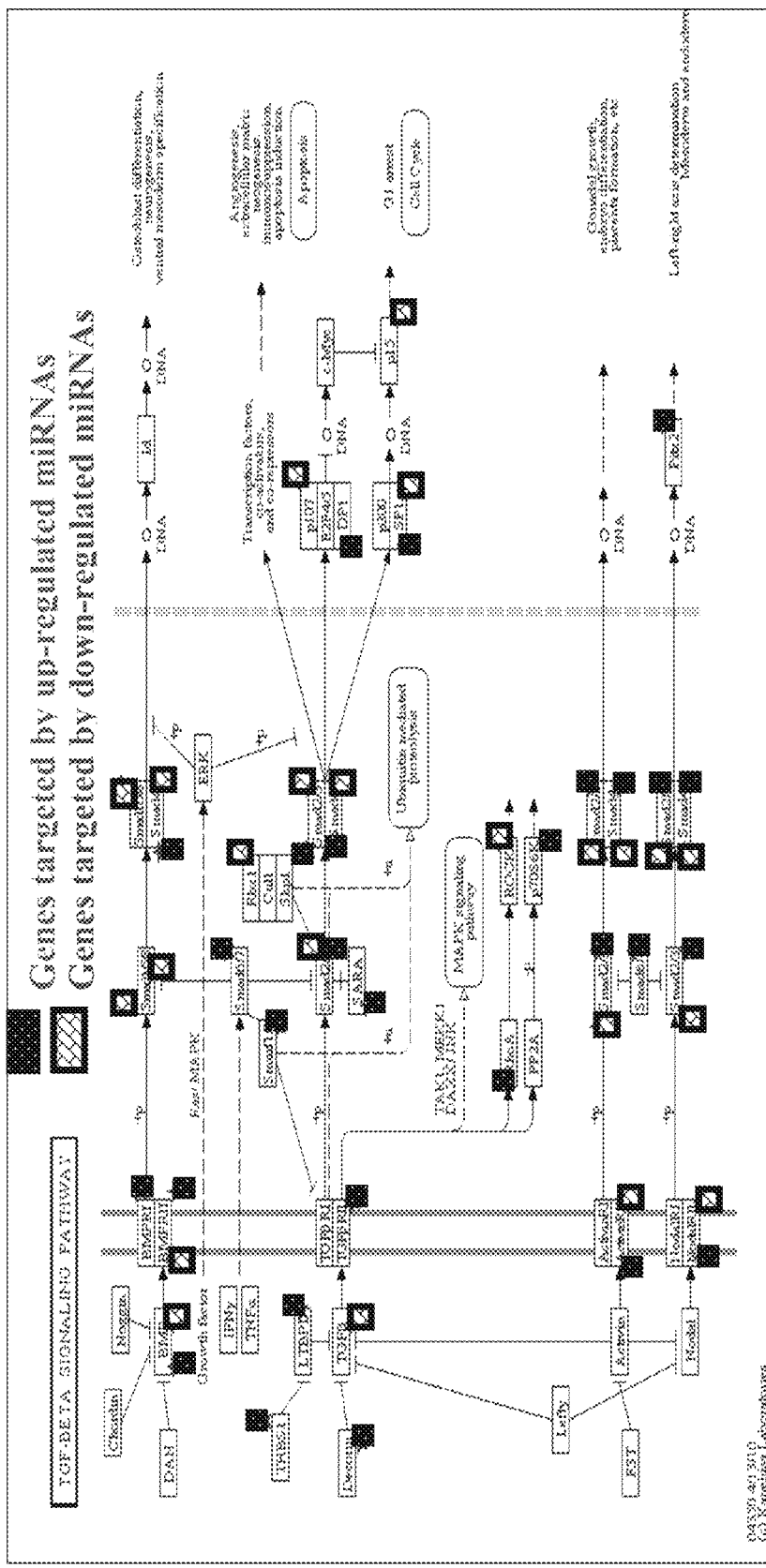
FIG. 2 is a diagram that shows the complex regulatory network of miRNAs on their osteogenic target genes in the TGF-Beta signaling pathway. Genes targeted by up-regulated miRNAs as shown. Genes targeted by down-regulated miRNAs as shown.
Figure 3:
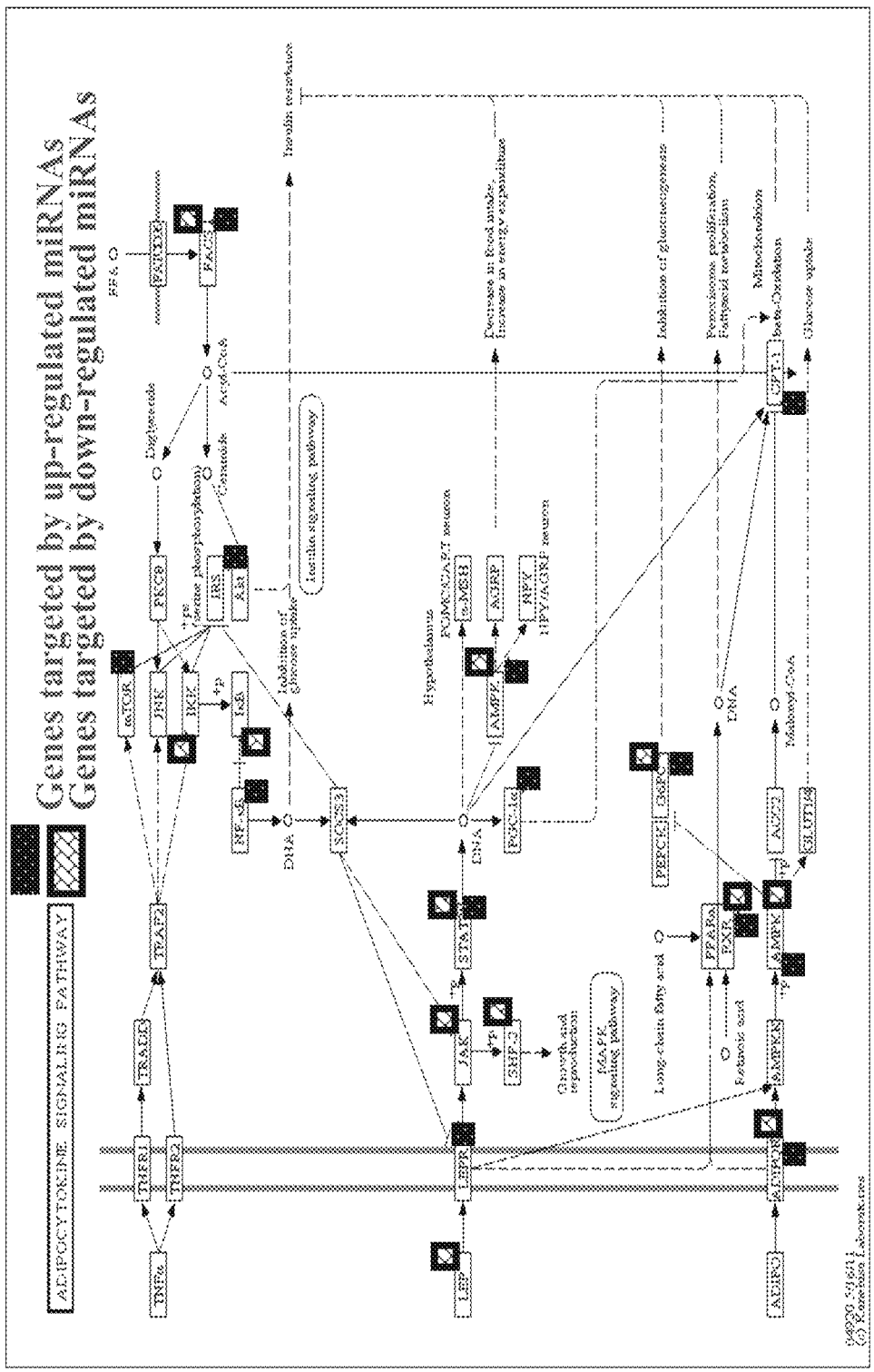
FIG. 3 is a diagram that shows complex regulatory network of miRNAs on their adipogenic target genes in the adipocytokine signaling pathway. Genes targeted by up-regulated miRNAs as shown. Genes targeted by down-regulated miRNAs as shown.

As used herein, "treat" means to prevent, reduce, decrease, or ameliorate one or more symptoms, or characteristics of a musculoskeletal disease and disorder, particular an age-related musculoskeletal diseases and disorders.

The terms "individual," "subject," and "patient" are used interchangeably herein, and refer to a mammal, including, but not limited to, rodents, simians, and humans.

The terms "reduce", "inhibit", "alleviate" and "decrease" are used relative to a control. One of skill in the art would readily identify the appropriate control to use for each experiment. For example a decreased response in a subject or cell treated with a compound is compared to a response in subject or cell that is not treated with the compound.

As used herein, the terms "inhibitors" or "antagonists" refers to compounds or compositions that directly or indirectly partially or totally block activity, decrease, prevent, delay activation, inactivate, desensitize, or down regulate the activity or expression of the targeted molecule. Antagonists are, for example, polypeptides, such as antibodies, as well as nucleic acids such as siRNA or antisense RNA, as well as naturally occurring and synthetic antagonists, including small chemical molecules.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art.

It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "endogenous" with regard to a nucleic acid or protein refers to nucleic acids or proteins normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions

It has been discovered that at least six miRNAs (miR-579,-1244,-374ab,-671-5p,-370,-29abcd) are up-regulated in aged BMSCs. Accordingly, compositions for decreasing expression of miR-579,-1244,-374ab,-671-5p,-370,-29abcd, or combinations thereof are disclosed. Typically, the composition includes an antagonist that reduces transcription or activity of miR-579,-1244,-374ab,-671-5p,-370,-29abcd, or combinations thereof. In some embodiments, the antagonist inhibits a transcription factor that regulates transcription of miR-579,-1244,-374ab,-671-5p,-370,-29abcd, or combinations thereof.

A. Antagonists of miRNA Upregulated in Aged BMSCs

1. Functional Nucleic Acids

In some embodiments, the antagonist is a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include, but are not limited to, antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the IQ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, A., et al. (1998) Nature, 391: 806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494-498) (Ui-Tei, K., et al. (2000) FEBS Lett. 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed transferases.

Therefore, in some embodiment the antagonist is a functional nucleic acid designed to target a glucuronoslytransferase or killer epitope-1 sulfotransferase (HNK-1ST). For example, antisense oligonucleotides, RNAi, dsRNA, miRNA, siRNA, external guide sequences, and the like can be designed to target a glucuronoslytransferase or killer epitope-1 sulfotransferase.

In some embodiments, the antisense oligonucleotide, RNAi, dsRNA, miRNA, siRNA, external guide sequence is designed to target a FINK-1ST that can reduce or inhibit expression of the nucleic acid sequence of miR-579,-1244,-374ab,-671-5p,-370, or -29abcd, or variant thereof having 70%, 75%, 80%, 85%, 90%, 95%, 97%, 99% or more sequence identity to miR-579,-1244,-374ab,-671-5p,-370, or -29abcd.

a. Antisense Inhibitors

In a particular embodiment, the inhibitory nucleic acids are antisense nucleic acids. The miRNA antagonists form a duplex with target miRNAs, which prevents the miRNA from binding to its target mRNA. This results in increased translation of the mRNA that is targeted by the miRNA.

The disclosed miRNA antagonists are single-stranded, double stranded, partially double stranded or hairpin structured oligonucleotides that include a nucleotide sequence sufficiently complementary to hybridize to a selected miRNA or pre-miRNA target sequence. As used herein, the term "partially double stranded" refers to double stranded structures that contain less nucleotides than the complementary strand. In general, partially double stranded oligonucleotides will have less than 75% double stranded structure, preferably less than 50%, and more preferably less than 25%, 20% or 15% double stranded structure.

An miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation.

Given the sequence of an miRNA or a pre-miRNA, an miRNA antagonist that is sufficiently complementary to a portion of the miRNA or a pre-miRNA can be designed according to the rules of Watson and Crick base pairing. As used herein, the term "sufficiently complementary" means that two sequences are sufficiently complementary such that a duplex can be formed between them under physiologic conditions. An miRNA antagonist sequence that is sufficiently complementary to an miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In a preferred embodiment, the miRNA antagonist is 100% complementary to an miRNA or pre-miRNA target sequence.

In some embodiments, the miRNA antagonist is sufficiently complementary to a portion of the miRNA or pre-miRNA sequence of a human miRNA disclosed herein. Sequences for miRNAs are available publicly, for example, through the miRBase registry (Griffiths-Jones, et al., *Nucleic Acids Res.*, 36 (Database Issue):D154-D158 (2008); Griffiths-Jones, et al., *Nucleic Acids Res.*, 36 (Database Issue): D140-D144 (2008); Griffiths-Jones, et al., *Nucleic Acids Res.*, 36 (Database Issue):D109-D111 (2008)) and other publically accessible databases.

In preferred embodiments, the miRNA antagonist is sufficiently complementary to a portion of the miRNA or pre-miRNA sequence of a human miRNA selected from miR-579,-1244,-374ab,-671-5p,-370, or -29abcd, or variant thereof having 70%, 75%, 80%, 85%, 90%, 95%, 97%, 99% or more sequence identity to miR-579,-1244,-374ab,-671-5p,-370, or -29abcd.

The miRNA antagonist can have a region that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementary to a portion of the miRNA or pre-miRNA sequence of a human miRNA selected from miR-579,-1244,-374ab,-671-5p,-370, or -29abcd, or variant thereof having 70%, 75%, 80%, 85%, 90%, 95%, 97%, 99% or more sequence identity to miR-579,-1244,-374ab,-671-5p,-370, or -29abcd.

Useful miRNA antagonists include oligonucleotides having at least 6, 7, 8, 9, 10, 11, 12, 13, 14, 15, 16, 17, 18, 19, 20 or more contiguous nucleotides substantially complementary to an endogenous miRNA or pre-miRNA of miR-579,-1244,-374ab,-671-5p,-370, or -29abcd, or variant thereof having 70%, 75%, 80%, 85%, 90%, 95%, 97%, 99% or more sequence identity to miR-579,-1244,-374ab,-671-5p,-370, or -29abcd. The disclosed miRNA antagonists preferably include a nucleotide sequence sufficiently complementary to hybridize to an miRNA target sequence of about 12 to 25 nucleotides, preferably about 15 to 23 nucleotides.

In some embodiments, there will be nucleotide mismatches in the region of complementarity. In a preferred embodiment, the region of complementarity will have no more than 1, 2, 3, 4, or 5 mismatches.

In some embodiments, the miRNA antagonist is "exactly complementary" to a human miRNA selected from miR-579,-1244,-374ab,-671-5p,-370, or -29abcd, or variant thereof having 70%, 75%, 80%, 85%, 90%, 95%, 97%, 99% or more sequence identity to miR-579,-1244,-374ab,-671-5p,-370, or -29abcd. Thus, in one embodiment, the miRNA antagonist can anneal to the miRNA to form a hybrid made exclusively of Watson-Crick base pairs in the region of exact complementarity. Thus, in some embodiments, the miRNA antagonist specifically discriminates a single-nucleotide difference. In this case, the miRNA antagonist only inhibits miRNA activity if exact complementarity is found in the region of the single-nucleotide difference.

In one embodiment, the miRNA antagonists are oligomers or polymers of ribonucleic acid (RNA) or deoxyribonucleic acid (DNA) or modifications thereof miRNA antagonists include oligonucleotides that contain naturally-occurring nucleobases, sugars and covalent internucleoside (backbone) linkages.

b. Antagomirs

In some embodiments, the miRNA antagonists are antagomirs. Antagomirs are a specific class of miRNA antagonists that are described, for example, in US2007/0213292 to Stoffel et al. Antagomirs are RNA-like oligonucleotides that contain various modifications for RNase protection and pharmacologic properties such as enhanced tissue and cellular uptake. Antagomirs differ from normal RNA by having complete 2′-O-methylation of sugar, phosphorothioate backbone and a cholesterol-moiety at 3′-end.

Antagomirs can include a phosphorothioate at least the first, second, or third internucleotide linkage at the 5′ or 3′ end of the nucleotide sequence. In one embodiment, antagomirs contain six phosphorothioate backbone modifications; two phosphorothioates are located at the 5′-end and four at the 3′-end. Phosphorothioate modifications provide protection against RNase activity and their lipophilicity contributes to enhanced tissue uptake.

Examples of antagomirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, all of which are hereby incorporated by reference.

Custom designed Anti-miR™ molecules are commercially available from Applied Biosystems. Thus, in some embodiments, the antagomir is an Ambion® Anti-miR™ inhibitor. These molecules are chemically modified and optimized single-stranded nucleic acids designed to specifically inhibit naturally occurring mature miRNA molecules in cells.

Custom designed Dharmacon Meridian™ microRNA Hairpin Inhibitors are also commercially available from Thermo Scientific. These inhibitors include chemical modifications and secondary structure motifs. For example, Vermeulen et al. reports in US2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

4. Small Molecules

The term "small molecule" generally refers to small organic compounds having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. The small molecules can include cyclical carbon or heterocyclic structures and/or aromatic or polyaromatic structures substituted with one or more functional groups. The small molecule antagonist reduces or interferes with expression or production of miR-579,-1244,-374ab,-671-5p,-370, or -29abcd, or a transcription factor thereof. In a preferred embodiment, the small molecule reduces or interferes with expression or function of miR-579,-1244,-374ab,-671-5p,-370, or -29abcd, or a transcription factor thereof.

B. Agonists of Genes Targeted by Up-Regulated miRNAs

Predicted bone homeostasis targets of miR-579,-1244,-374ab,-671-5p,-370, or -29abcd include SDF-1, BMP2, β arrestin, SOX4, Leptin, IGF-1, VEGF, Collagen type 1 α1 and α2. Accordingly compositions for increasing expression of genes that are targeted for degradation by miRNAs up-regulated in aged BMSCs are also disclosed. Expression of target genes can be up-regulated by increasing expression of transcription factors, for example, transcription factors that increase expression of SDF-1, BMP2, β arrestin, SOX4, Leptin, IGF-1, VEGF, Collagen type 1 α1 and α2, or combinations thereof. In another embodiments, expression vectors encoding SDF-1, BMP2, β arrestin, SOX4, Leptin, IGF-1, VEGF, Collagen type 1 α1 or a2 are transfected into cells, for example BMSCs.

Vectors and constructs containing a gene, mRNA, or cDNA, encoding SDF-1, BMP2, β arrestin, SOX4, Leptin, IGF-1, VEGF, Collagen type 1 α1 and α2, or combinations thereof operably linked to an endogenous or heterologous expression control sequence are also provided. The constructs can include an expression cassette containing SDF-1, BMP2, β arrestin, SOX4, Leptin, IGF-1, VEGF, Collagen type 1 α1 or α2, gene, mRNA, cDNA, or variant or fragment thereof.

Transformation constructs can be engineered such that transformation of the nuclear genome and expression of transgenes from the nuclear genome occurs. An exemplary construct contains a nucleic acid sequence encoding SDF-1, BMP2, β arrestin, SOX4, Leptin, IGF-1, VEGF, Collagen type 1 α1 or α2, operatively linked in the 5' to 3' direction to a promoter that directs transcription of the nucleic acid sequence, and a 3' polyadenylation signal sequence.

Generally, nucleic acid sequences are first assembled in expression cassettes behind a suitable promoter. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments.

In some embodiments, the agonist is a polypeptide including the amino acid sequence of SDF-1, BMP2, β arrestin, SOX4, Leptin, IGF-1, VEGF, Collagen type 1 α1 or α2. In some embodiments, the polypeptide is a fusion protein. For example, in some embodiments the polypeptide also includes a protein transduction domain to increase passage of the polypeptide into the cell.

In some embodiments, the agonist is mRNA encoding SDF-1, BMP2, β arrestin, SOX4, Leptin, IGF-1, VEGF, Collagen type 1 α1 or α2. mRNA can be transfected into a cell to transiently increase expression of SDF-1, BMP2, β arrestin, SOX4, Leptin, IGF-1, VEGF, Collagen type 1 α1 or α2.

C. Agonists of miRNA Down-Regulated in Aged BMSCs

It has been discovered that at least 11 miRNAs including miR-1231,-517-ac,-3180-5p are reduced in aged hBMSCs. Accordingly, compositions for decreasing expression of miR-1231,-517-ac,-3180-5p, or other down-regulated miRNA in aged BMSCs, or combinations thereof are disclosed. Other miRNA down-regulated in aged BMSCs are discussed in the Figures and Examples below. In some embodiments, the agonist of miR-1231,-517-ac,-3180-5p, and other down-regulated miRNA in aged BMSCs disclosed herein is an agonist that increases expression of the endogenous miR-1231,-517-ac,-3180-5p, or other down-regulated miRNA in aged BMSCs disclosed herein. In some embodiments, the agonist is a vector encoding the miRNA. Suitable vectors and cloning methods are discussed above.

In preferred embodiments, the agonist is the miRNA itself. The miRNA can be isolated from cells or tissues, recombinantly produced, or synthesized in vitro by a variety of techniques well known to one of ordinary skill in the art. In one embodiment, miRNA is isolated from cells or tissues. Techniques for isolating miRNA from cells or tissues are well known to one of ordinary skill in the art. For example, miRNA can be isolated from total RNA using the mirVana miRNA isolation kit from Ambion, Inc. Another techniques utilizes the flashPAGE™ Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This embodiment involves growing a culture of host cells in a suitable culture medium, and purifying the miRNA from the cells or the culture in which the cells are grown. For example, the methods include a process for producing an miRNA in which a host cell containing a suitable expression vector that includes a nucleic acid encoding an miRNA is cultured under conditions that allow expression of the encoded miRNA. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE, dextran mediated transfection, or electroporation (Davis, L. et al., *Basic Methods in Molecular Biology* (1986)).

Any host/vector system can be used to express one or more of the miRNAs. These include eukaryotic hosts such as HeLa cells and yeast, as well as prokaryotic host such as *E. coli* and *B. subtilis*. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter, polyadenylation site, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Potentially suitable yeast strains include *Saccharomyces cerevisiae, Schizosaccharomyces pombe, Kluyveromyces* strains, *Candida*, or any yeast strain capable of expressing miRNA. Potentially suitable bacterial strains include *Escherichia coli, Bacillus subtilis, Salmonella typhimurium*, or any bacterial strain capable of expressing miRNA.

In a preferred embodiment, genomic DNA encoding the miRNA is isolated, the genomic DNA is expressed in a mammalian expression system, and RNA is purified and modified as necessary for administration to an individual.

Knowledge of DNA sequences of miRNA allows for modification of cells to permit or increase expression of an endogenous miRNA. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al.

The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, heparin-Toyopearl™ or Cibacrom blue 3GA Sepharose™; one or more steps involving hydrophobic interaction chromatography using such resins as phenyl ether, butyl ether, or propyl ether; immunoaffinity chromatography, or complementary cDNA affinity chromatography.

The miRNA may also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science 244:1288-1292 (1989)), such that the express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In a preferred embodiment, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro phosphorothioate internucleoside linkages are well known in the art (see Uhlmann et al., 1990, *Chem. Rev.* 90:543-584; Schneider et al., 1990, *Tetrahedron Lett.* 31:335 and references cited therein). U.S. Pat. Nos. 5,614,617 and 5,223,618 to Cook, et al., U.S. Pat. No. 5,714,606 to Acevedo, et al., U.S. Pat. No. 5,378,825 to Cook, et al., U.S. Pat. No. 5,672,697 and U.S. Pat. No. 5,466,786 to Buhr, et al., U.S. Pat. No. 5,777,092 to Cook, et al., U.S. Pat. No. 5,602,240 to De Mesmaeker, et al., U.S. Pat. No. 5,610,289 to Cook, et al. and U.S. Pat. No. 5,858,988 to Wang, also describe nucleic acid analogs for enhanced nuclease stability and cellular uptake.

D. Antagonists of Genes Target by Down-Regulated miRNAs

It has been discovered that predicted targets of miRNAs down-regulated in aged BMSCs included adipogenic genes such as PPAR-gamma or -alpha, AP2-alpha, CD36, and others disclosed in the Examples and Figures herein. Accordingly, in some embodiments, the compositions include an antagonist of PPAR-gamma or -alpha, AP2-alpha, CD36, and others genes targeted by miRNAs down-regulated in aged BMSCs. Antagonists can includes, for example functional nucleic acids or small molecules that target PPAR-gamma or -alpha, AP2-alpha, CD36, and others genes targeted by miRNAs down-regulated in aged BMSCs. Functional nucleic acids and small molecules are described above.

E. Nucleic Acid Compositions

In some embodiments, the disclosed agonists and antagonists are nucleic acids. The nucleic acids can be composed of naturally occurring nucleotides or modified nucleotides. Exemplary modifications are provided below.

1. Bases

The nucleic acids can contain modified bases. Adenine, guanine, cytosine and uracil are the most common bases found in RNA. These bases can be modified or replaced to provide RNAs having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine). Alternatively, substituted or modified analogs of any of the above bases can be used. Examples include, but are not limited to, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxy-acetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl) uracil, 3-methylcytosine, 5-methylcytosine, N4-acetyl cytosine, 2-thiocytosine, N6-methyladenine, N6-isopentyladenine, 2-methylthio-N-6-isopentenyladenine, N-methylguanines, or O-alkylated bases.

The disclosed nucleic acids can be modified to enhanced resistance to nucleases. Thus, the disclosed nucleic acids can be an oligomer that includes nucleotide modification that stabilized it against nucleolytic degradation. The oligomer can be a totalmer, mixmer, gapmer, tailmer, headmer or blockmer. A "totalmer" is a single stranded oligonucleotide that only comprises non-naturally occurring nucleotides. The term "gapmer" refers to an oligonucleotide composed of modified nucleic acid segments flanking at least 5 naturally occurring nucleotides (i.e., unmodified nucleic acids). The term "blockmer" refers to a central modified nucleic acid segment flanked by nucleic acid segments of at least 5 naturally occurring nucleotides. The term "tailmer" refers to an oligonucleotide having at least 5 naturally occurring nucleotides at the 5'-end followed by a modified nucleic acid segment at the 3'-end. The term "headmer" refers to oligonucleotide having a modified nucleic acid segment at the 5'-end followed by at least 5 naturally occurring nucleotides at the 3'-end. The term "mixmer" refers to oligonucleotide which comprise both naturally and non-naturally occurring nucleotides. However, unlike gapmers, tailmers, headmers and blockmers, there is no contiguous sequence of more than 5 naturally occurring nucleotides, such as DNA units.

Modified nucleic acids and nucleotide surrogates can include one or more of: (i) replacement of one or both of the non-linking phosphate oxygens and/or of one or more of the linking phosphate oxygens; (ii) replacement of a constituent of the ribose sugar, e.g., of the 2' hydroxyl on the ribose sugar, or wholesale replacement of the ribose sugar with a structure other than ribose; (iii) wholesale replacement of the phosphate moiety with "dephospho" linkers; (iv) modification or replacement of a naturally occurring base; (v) replacement or modification of the ribose-phosphate backbone; or (vi) modification of the 3' end or 5' end of the RNA, e.g., removal, modification or replacement of a terminal phosphate group or conjugation of a moiety, such as a fluorescently labeled moiety, to either the 3' or 5' end of RNA.

2. The Sugar Group

The nucleic acids can contain modified sugar groups. For example, the 2' hydroxyl group (OH) can be modified or replaced with a number of different "oxy" or "deoxy" substitutents.

Examples of "oxy"-2' hydroxyl group modifications include alkoxy or aryloxy, "locked" nucleic acids (LNA) in which the 2' hydroxyl is connected, for example, by a methylene bridge or ethylene bridge to the 4' carbon of the same ribose sugar; amino, O-AMINE and aminoalkoxy. Oligonucleotides containing only methoxyethyl groups (MOE) exhibit nuclease stabilities comparable to those modified with the robust phosphorothioate modification.

"Deoxy" modifications include hydrogen, halo, amino, cyano; mercapto, alkyl-thio-alkyl, thioalkoxy, and alkyl, cycloalkyl, aryl, alkenyl and alkynyl, which may be optionally substituted. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Also included are "abasic" sugars, which lack a nucleobase at C-1'. These abasic sugars can also contain additional modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

3. The Phosphate Group

The disclosed nucleic acids can contain modified phosphate groups. The phosphate group is a negatively charged species. The charge is distributed equally over the two non-linking oxygen atoms. However, the phosphate group can be modified by replacing one of the oxygens with a different substituent. One result of this modification to RNA phosphate backbones can be increased resistance of the oligoribonucleotide to nucleolytic breakdown.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species.

The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Oligonucleotide-mimicking scaffolds can also be constructed wherein the phosphate linker and ribose sugar are replaced by nuclease resistant nucleoside or nucleotide surrogates. Examples include the mophilino, cyclobutyl, pyrrolidine and peptide nucleic acid (PNA) nucleoside surrogates. A preferred surrogate is a PNA surrogate.

4. Terminal Modifications

The disclosed nucleic acids can also be modified at their 3' and/or 5' ends. Terminal modifications can be added for a number of reasons, including to modulate activity, to modulate resistance to degradation, or to modulate uptake of the nucleic acids by cells. Modifications can include modification or replacement of an entire terminal phosphate or of one or more of the atoms of the phosphate group. For example, the 3' and 5' ends of an oligonucleotide can be conjugated to other functional molecular entities such as labeling moieties or protecting groups. The functional molecular entities can be attached to the sugar through a phosphate group and/or a spacer. The terminal atom of the spacer can connect to or replace the linking atom of the phosphate group or the C-3' or C-5' 0, N, S or C group of the sugar. Alternatively, the spacer can connect to or replace the terminal atom of a nucleotide surrogate. Other examples of terminal modifications include dyes, intercalating agents, cross-linkers, porphyrins, polycyclic aromatic hydrocarbons, artificial endonucleases, lipophilic carriers and peptide conjugates.

III. Methods of Treatment or Prevention

A. Disorders to be Treated

Musculoskeletal diseases and disorders, particularly age-related musculoskeletal diseases and disorders can be treated. The compositions described herein can be administered in effective dosages, alone or in combination with a second therapeutic, to improve at least one symptom or manifestation of the disease. As used herein, "improve" means to inhibit the rate of development, stop development, or reverse development of a symptom or characteristic of the disorder. The compositions can be used to treat, alleviate, reduce, or inhibit a musculoskeletal disease and disorder, particular an age-related musculoskeletal diseases and disorders, senescence, or symptoms thereof.

Exemplary musculoskeletal diseases and disorders include but are not limited to low back pain, pain in the pain in the shoulder, elbow, hip, neck, or foot pain, osteoarthritis, osteoporosis, tendinitis, bursitis, gout, fibromyalgia, rheumatoid arthritis, degenerative changes to muscles, tendons, ligaments, and/or joints, reduced strength and sacropenia. In some embodiments, the disease or disorder causes pain in muscular or tendinous areas of the extremities but not in joints such as, for example, soft tissue rheumatism. A preferred disease to be treated includes but is not limited to osteoporosis, in particular, age-related osteoporosis.

In some embodiments, the subject is at least 30, 35, 40, 45, 50, 55, 60, 65, 70, 75, 80, 85, 90, or 95 years in age. The subject can be in an age range, for example, the subject can be between 30 and 90 years old, between 35 and 85 years old, between 40 and 80 years old, between 45 and 75 years old, between 50 and 70 years old, or between 55 and 65 years old. In some embodiments the subject is 45-65 years old, 60-65 years old, or 50-70 years old.

In addition, compounds disclosed herein can be used for prophylactic treatment of a musculoskeletal disease or disorder, particular an age-related musculoskeletal disease or disorder. Under these circumstances, it may be beneficial to treat these individuals with therapeutically effective doses of the nucleic acids or modulators to reduce the risk of developing a musculoskeletal disease or disorder, particular an age-related musculoskeletal disease or disorder. In other embodiments, the nucleic acid or modulator in a suitable formulation is administered to a subject who has reached a particular age, for example age 40 or more. In yet other embodiments, the nucleic acid or modulator in a suitable formulation is administered to subjects who exhibit symptoms of a musculoskeletal disease or disorder, particular an age-related musculoskeletal disease or disorder. In still other embodiments, the nucleic acid in a suitable formulation may be administered to a subject as a preventive measure. In some embodiments, the nucleic acid or modulator is in a suitable formulation may be administered to a subject based on demographics or epidemiological studies, or to a subject in a particular field or career.

B. Formulations

The compounds are preferably employed for therapeutic uses in combination with a suitable pharmaceutical carrier. Such compositions comprise an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein.

It is understood by one of ordinary skill in the art that nucleic acids administered in vivo are taken up and distributed to cells and tissues (Huang, et al., *FEBS Lett.* 558(1-3): 69-73 (2004)). For example, Nyce et al. have shown that antisense oligodeoxynucleotides (ODNs) when inhaled bind to endogenous surfactant (a lipid produced by lung cells) and are taken up by lung cells without a need for additional carrier lipids (Nyce and Metzger, *Nature*, 385:721-725 (1997). Small nucleic acids are readily taken up into T24 bladder carcinoma tissue culture cells (Ma, et al., *Antisense Nucleic Acid Drug Dev.* 8:415-426 (1998). siRNAs have been used for therapeutic silencing of an endogenous genes by systemic administration (Soutschek, et al., *Nature* 432, 173-178 (2004)).

The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Various methods for nucleic acid delivery are described, for example in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition. The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. For administration by inhalation, the compound are conveniently delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the compound are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.* 14(19):4975-4977 (2004)) and in vivo (Soutschek, et al., *Nature* 432(7014):173-178 (2004)). In addition, it has been shown that binding of steroid conjugated oligonucleotides to different lipoproteins in the bloodstream, such as LDL, protect integrity and facilitate biodistribution (Rump, et al., *Biochem. Pharmacol.* 59(11):1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe (II) and porphyrin-Fe(II); alkylating moieties,; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also described methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

The formulations described herein of the nucleic acids embrace fusions of the nucleic acids or modifications of the nucleic acids, wherein the nucleic acid is fused to another moiety or moieties, e.g., targeting moiety or another therapeutic agent. Such analogs may exhibit improved properties such as activity and/or stability. Examples of moieties which may be linked or unlinked to the nucleic acid include, for example, targeting moieties which provide for the delivery of nucleic acid to specific cells, e.g., antibodies to pancreatic cells, immune cells, lung cells or any other preferred cell type, as well as receptor and ligands expressed on the preferred cell type.

Formulations for oral delivery are also disclosed. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc., or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also, Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The composition can be chemically modified so that oral delivery of the compound is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

For oral formulations, the location of release may be the stomach, the small intestine (the duodenum, the jejunum, or the ileum), or the large intestine. Preferably, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

Compositions for oral delivery of nucleic acids are known in the art and discussed, for example, in Kriegel, et al., *Adv. Drug Deliv. Rev.* 15; 65(6):891-901 (2013), which discuss the utilization of multi-compartmental delivery systems such as solid nanoparticles-in-microsphere, solid nanoparticles-in-emulsion, and liquid nanoparticles-in-emulsion. An exemplary delivery vehicle is type B gelatin nanoparticles encapsulated in poly(ε-caprolactone) microspheres. The results of the studies show that the multi-compartmental formulations can overcome many of the barriers for effective oral nucleic acid delivery.

D. Controlled Release Formulations

Controlled or sustained release can be achieved by the addition of time-release additives, such as polymeric structures, matrices, that are available in the art.

For example, the compositions can be delivered using a sustained release device. Either non-biodegradable or biodegradable matrices can be used for delivery of nucleic acids, although biodegradable matrices are preferred. These may be natural or synthetic polymers, although synthetic polymers are preferred due to the better characterization of degradation and release profiles. The polymer is selected based on the period over which release is desired, generally in the range of at least two to six weeks, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

Oligonucleotides can be delivered partially by diffusion but mainly by degradation of the polymeric system. In this case, biodegradable polymers, bioerodible hydrogels, and protein delivery systems are particularly preferred. Examples of non-biodegradable polymers include ethylene vinyl acetate, poly(meth)acrylic acid, polyamides, copolymers and mixtures thereof. Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In one embodiment, the polymeric matrix is in the form of microparticles or nanoparticles. Microparticles can be in the form of microspheres, where the composition is dispersed within a solid polymeric matrix, or microcapsules, where the core is of a different material than the polymeric shell, and the composition is dispersed or suspended in the core, which may be liquid or solid in nature. Unless specifically defined herein, microparticles, microspheres, microcapsules, nanoparticles, nanospheres, and nanocapsules are used interchangeably.

Alternatively, the polymer may be cast as a thin slab or film, ranging from nanometers to four centimeters, a powder produced by grinding or other standard techniques, or even a gel such as a hydrogel. The matrices can be formed by solvent evaporation, spray drying, solvent extraction and other methods known to those skilled in the art.

Another embodiment provides compositions incorporated in a conventional hydrophobic polymer matrix, e.g. of a polylactide, which is made more accessible for water by introducing a hydrophilic unit, e.g. of polyethyleneglycol, polyvinylalcohol, dextran or polymethacrylamide. The hydrophilic contribution to the amphipathic polymer is given by all the ethylene oxide groups in case of a polyethylene glycol unit, by the free hydroxyl groups in the case of a polyvinylalcohol unit or of a dextran unit, and by the amide groups in the case of a polymethyacrylamide unit.

D. Methods of Administration

In general, methods of administering compounds, including nucleic acids, are well known in the art. In particular, the routes of administration already in use for nucleic acid therapeutics, along with formulations in current use, provide preferred routes of administration and formulation for the nucleic acids described above.

Compositions can be administered by a number of routes including, but not limited to: oral, intravenous, intraperitoneal, intramuscular, transdermal, subcutaneous, topical, sublingual, or rectal means. Compounds can also be administered via liposomes. Such administration routes and appropriate formulations are generally known to those of skill in the art.

Administration of the formulations described herein may be accomplished by any acceptable method which allows the compounds, for example miRNA or nucleic acid encoding the miRNA, to reach its target. The particular mode selected will depend of course, upon factors such as the particular formulation, the severity of the state of the subject being treated, and the dosage required for therapeutic efficacy. As generally used herein, an "effective amount" is that amount which is able to treat one or more symptoms of age related disorder, reverse the progression of one or more symptoms of age related disorder, halt the progression of one or more symptoms of age related disorder, or prevent the occurrence of one or more symptoms of age related disorder in a subject to whom the formulation is administered, as compared to a matched subject not receiving the compound. The actual effective amounts of compound can vary according to the specific compound or combination thereof being utilized, the particular composition formulated, the mode of administration, and the age, weight, condition of the individual, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intradermally for treatment or prevention of age related disorder, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets Inhalation includes administering the composition with an aerosol in an inhaler, either alone or attached to a carrier that can be absorbed. For systemic administration, it may be preferred that the composition is encapsulated in liposomes.

The nucleic acid may be delivered in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

E. Effective Dosages

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to an individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the miRNA employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

Therapeutic compositions comprising one or more nucleic acids or modulator are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the $LD_{50}$ of the relevant formulation, and/or observation of any side-effects of the nucleic acids at various concentrations, e.g., as applied to the mass and overall health of the individual. Administration can be accomplished via single or divided doses.

In vitro models can be used to determine the effective doses of the nucleic acids or modulator as a potential age related disorder treatment, as described in the examples. In determining the effective amount of the compound to be administered in the treatment or prophylaxis of disease the physician evaluates circulating plasma levels, formulation toxicities, and progression of the disease. For nucleic acids, the dose administered to a 70 kilogram individual is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-age-related disorder cocktail. Anti-ageing cocktails can include, therapeutics to treat Alzheimer's disease, Parkinson's disease, stroke, high blood pressure, dementia, heart disease, and arthritis.

F. Cell Therapy

In some embodiments, target cells are first isolated from a donor using methods known in the art, contacted with one or more of the nucleic acids or modulators disclosed herein in vitro (ex vivo), and administered to a patient in need thereof. Sources or cells include, but are not limited to BMSCs can be harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

In some embodiments the cells are contacted with one or more of the compositions disclosed herein. This method can be used to prepare universal donor cells.

For example, a method of treating an age-related musculoskeletal disease or disorder in a subject can include treating isolated human bone marrow mesenchymal stromal cells ex vivo with a composition including an agent that decreases expression or bioavailability of an miRNA selected from the group consisting of miR-579, miR-1244, miR-374ab, miR-671-5p, miR-370, miR-29abcd, or combinations thereof, or increase expression or bioavailability of an miRNA selected from the group consisting of miR-1231, miR-517-ac, and miR-3180-5p. The agent can be effective increase expression of SDF-1, BMP2, β arrestin, SOX4, Leptin, IGF-1, VEGF, Collagen type 1 α1 or Collagen type 1 α2, or decrease expression of PPAR-gamma, PPAR-alpha, AP2-alpha, or CD36 in the cells. The treated cells can be administered to the subject to reduce one or more symptoms of the age-related musculoskeletal disease or disorder. The isolated cells can be reprogrammed ex vivo to alter the miRNA expression profile of the cells to be more similar to the miRNA expression profile of cells isolated from subjects from 29-41 years of age than untreated cells.

EXAMPLES

Example 1

Materials and Methods

Isolation of CD271+Human BMSCs from Bone Marrow Aspirates

In order to avoid potential tissue culture driven changes in BMSC miRNA, mRNA and protein expression patterns associated with cell passage, a direct-isolation procedure was used to quickly capture human BMSCs directly from bone marrow without culturing or standard plastic adherence based isolation. Bone marrow was obtained from Orthopedic surgery patients as per IRB approved from "waste" material that would normally be discarded. Samples were collected from patients aged between 21-75. EDTA was added to prevent clotting. CD271 has been shown to be a suitable marker for the enrichment of non-hematopoietic stem cells from bone marrow aspirates [1,2].

The CD271+BMSCs were isolated according to the manufacturer's protocol by using a kit (CD271 (APC) MicroBead Kit, Miltenyi Biotec Inc. CA. Cat #130-092-283). Briefly, from the BM samples, the mononuclear cells were collected by density gradient separation using Ficoll-Paque. The cell number was determined by counting. The CD271+BMSCs were magnetically labeled using CD271 (LNGFR)-APC and Anti-APC microbeads. MS column was placed in the suitable magnetic field of MACS Separator.

The cell suspension was applied onto the column and the unlabeled cells were allowed to pass and the column was washed three times. The column was removed from the separator and placed it on a suitable collection tube. The highly enriched CD271+BMSCs were eluted and the cell number was determined.

Microarray Analysis

The total RNA was isolated from CD271+BMSCs according to the manufacturer's protocol by using a kit (miRNeasy Mini kit, Qiagen, Cat #217004).

Microarrays were performed using an Affymetrix GeneChip® miRNA 2.0 Array at the Integrated Genomics Core, Georgia Health Sciences University, Augusta, Ga. Three "young" patients (29-41 years of age) and four "old" patients (64-73 years of age) were assessed. Affymetrix GeneChip® miRNA 2.0 Arrays provide the most sensitive, accurate, and complete measurement of small non-coding RNA transcripts involved in gene regulation. The results were normalized using robust multichip average (RMA). The final results were assessed by 2-way ANOVA analysis of young vs old BMSCs (with sex and age as the variables) using the Partek Genomics Suite.

Results

Isolated human CD271+BMSCs by using a kit (CD271 (APC) MicroBead Kit, Miltenyi Biotec Inc. CA.) from surgical bone marrow specimens of three young (under 40 yrs old) and three old (over 75 yrs old) patients, without plastic adhesion or culturing that might alter miRNA and gene expression. Total RNA was isolated from the CD271+BMSCs and microarrays were performed using an Affymetrix GeneChip® miRNA 2.0 Array, normalized using robust multichip average (RMA), and assessed by 2-way ANOVA analysis of young vs old BMSCs (with sex and age as the variables) using the Partek Genomics Suite. This genome-wide assessment of miRNA expression revealed multiple miRNAs whose expressions were altered with age. Six miRNAs (miR-579,-1244,-374ab,-671-5p,-370,-29abcd) were identified that were significantly up-regulated in aged BMSCs. Predicted bone homeostasis targets of these miRNAs include SDF-1, BMP2, β arrestin, SOX4, Leptin, IGF-1, VEGF, Collagen type 1 α1 and a2. Eleven miRNAs including miR-1231,-517-ac,-3180-5p were identified that were significantly reduced in aged hBMSCs. Predicted targets of these miRNAs included adipogenic genes such as PPAR-gamma or -alpha, AP2-alpha, and CD36. These results indicate that the differential miRNA expression in BMSCs with age may regulate age-associated changes that reduce osteogenic capacity and increase the adipogenic fate of these stem cells, and may help drive the development of osteoporosis.

TABLE 1

Differential Expressing miRNAs and their Predicted Osteogenic Target Genes. Differential expression of miRNAs in Old CD271+ BMSCs versus young CD271+ BMSCs. The miRNA target genes were predicted by using 3 databases (Targetscan, miRDB, DIANA-microT).

| Target Transcript | Age-altered miRNA (⇑ = miR upregulated; ↓ = miR down-regulated) |
|---|---|
| CXCL12 | miR-29a-5p⇑ miR-1244⇑ |
| DPP4 | miR-3173-5p↓ |
| CXCR4 | miR-3120-3p↓ |
| b-Arrestin | miR-374ab-5p⇑ miR-579⇑ |
| S1P receptors | miR-374b-5p⇑ miR-374a-3p/5p⇑ miR-593-5p↓ |
| Leptin | miR-3180-5p↓ miR 671⇑ miR-370⇑ |
| Leptin receptor | miR-374ab-5p⇑ |
| IGF-1 | miR-29abc-3p⇑ miR-374a-3p⇑ miR-3120-3p↓ |
| IGF-1 receptors | miR-29a-5p⇑ miR-885-3p↓ miR-3180-5p↓ |
| BMP2 | miR-374ab-5p⇑ miR-1231↓; |
| BMP receptors | miR-374b-3p⇑ miR-374b-5p⇑ miR-1231↓ miR-374a-3p⇑ miR-3120-3p↓ miR-671⇑ miR-593-3p↓ miR-3120-3p↓ |
| PPARg | miR-370⇑ miR-1231↓ |

TABLE 2

Summary of Gene Ontology Biological Process Terms of Genes Targeted by Each miRNA Up-regulated with Age

| mir-29b | |
|---|---|
| GOTERM_BP_FAT | GO:0030199~collagen fibril organization |
| GOTERM_BP_FAT | GO:0007156~homophilic cell adhesion |
| GOTERM_BP_FAT | GO:0016337~cell-cell adhesion |
| GOTERM_BP_FAT | GO:0030198~extracellular matrix organization |
| GOTERM_BP_FAT | GO:0007155~cell adhesion |
| GOTERM_BP_FAT | GO:0022610~biological adhesion |
| GOTERM_CC_FAT | GO:0005581~collagen |
| GOTERM_CC_FAT | GO:0044420~extracellular matrix part |
| GOTERM_CC_FAT | GO:0005576~proteinaceous extracellular matrix |
| GOTERM_CC_FAT | GO:0031012~extracellular matrix |
| GOTERM_CC_FAT | GO:0005604~basement membrane |
| GOTERM_CC_FAT | GO:0005583~fibrillar collagen |
| GOTERM_CC_FAT | GO:0005588~collagen type V |
| GOTERM_CC_FAT | GO:0044421~extracellular region part |
| GOTERM_CC_FAT | GO:0005587~collagen type IV |
| KEGG_PATHWAY | hsa04510:Focal adhesion |
| KEGG_PATHWAY | hsa04512:ECM-receptor interaction |
| KEGG_PATHWAY | hsa05222:Small cell lung cancer |
| miR-370 | |
| GOTERM_BP_FAT | GO:0046330~positive regulation of JNK cascade |
| GOTERM_BP_FAT | GO:0048701~embryonic cranial skeleton morphogenesis |
| GOTERM_BP_FAT | GO:0007224~smoothened signaling pathway |
| GOTERM_BP_FAT | GO:0007167~enzyme linked receptor protein signaling pathway |
| GOTERM_BP_FAT | GO:0010033~response to organic substance |
| KEGG_PATHWAY | hsa05200:Pathways in cancer |
| KEGG_PATHWAY | hsa05215:Prostate cancer |
| KEGG_PATHWAY | hsa04910:Insulin signaling pathway |
| miR-374 | |
| GOTERM_BP_FAT | GO:0007267~cell-cell signaling |
| GOTERM_BP_FAT | GO:0030030~cell projection organization |
| GOTERM_BP_FAT | GO:0031175~neuron projection development |
| GOTERM_BP_FAT | GO:0030054~cell junction |
| KEGG_PATHWAY | hsa04350:TGF-beta signaling pathway |
| miR-579 | |
| GOTERM_BP_FAT | GO:0030030~cell projection organization |
| GOTERM_BP_FAT | GO:0048666~neuron development |

TABLE 2-continued

Summary of Gene Ontology Biological Process Terms
of Genes Targeted by Each miRNA Up-regulated with Age miR-671

| | |
|---|---|
| GOTERM_BP_FAT | GO:0006796~phosphate metabolic process |
| GOTERM_BP_FAT | GO:0006793~phosphorus metabolic process |
| GOTERM_BP_FAT | GO:0000096~sulfur amino acid metabolic process |
| GOTERM_BP_FAT | GO:0030500~regulation of bone mineralization | miR-1244

| | |
|---|---|
| GOTERM_BP_FAT | GO:0007173~epidermal growth factor receptor signaling pathway |
| GOTERM_BP_FAT | GO:0007169~transmembrane receptor protein tyrosine kinase signaling |
| GOTERM_BP_FAT | GO:0051496~positive regulation of stress fiber formation |
| GOTERM_CC_FAT | GO:0005581~collagen |

Table 2 shows clustering of predicted gene transcripts that individual up-regulated miRNAs target affects. Numerous individual genes and pathways in patterns associated with mesenchymal cells, collagens, bone mineralization, signaling pathways, biosynthetic and metabolic systems are affected by each miRNA.

Table 3 shows a functional enrichment cluster analysis performed with DAVID Bioinformatic Resources, which shows that in the "old" human BMSCs (vs the "young") there was a statistically significant up regulation of miRNAs that down-regulate clusters of genes associated with the skeletal system and its development.

TABLE 3

Functional Enrichment Cluster Analysis of Genes
targeted by miRNAs Up-regulated in Aged BMSCs

| | |
|---|---|
| Annotation Cluster 17 | Enrichment Score: 1.6917017351476866 |
| Category | Term |
| GOTERM_BP_FAT | GO:0008286~insulin receptor signaling pathway |
| GOTERM_BP_FAT | GO:0032870~cellular response to hormone stimulus |
| Annotation Cluster 18 | Enrichment Score: 1.6772690233874317 |
| Category | Term |
| GOTERM_BP_FAT | GO:0007267~cell-cell signaling |
| GOTERM_BP_FAT | GO:0007268~synaptic transmission |
| Annotation Cluster 19 | Enrichment Score: 1.620911780736517 |
| Category | Term |
| GOTERM_BP_FAT | GO:0030522~intracellular receptor-mediated signaling pathway |
| GOTERM_BP_FAT | GO:0030331~estrogen receptor binding |
| Annotation Cluster 20 | Enrichment Score: 1.5943854435411942 |
| Category | Term |
| GOTERM_BP_FAT | GO:0060538~skeletal muscle organ development |
| GOTERM_BP_FAT | GO:0007519~skeletal muscle tissue development |
| Annotation Cluster 21 | Enrichment Score: 1.5252241833588265 |
| Category | Term |
| KEGG_PATHWAY | hsa05215:Prostate cancer |
| KEGG_PATHWAY | hsa04012:ErbB signaling pathway |
| Annotation Cluster 22 | Enrichment Score: 1.4456372104219561 |
| Category | Term |
| GOTERM_BP_FAT | GO:0031644~regulation of neurological system process |
| GOTERM_BP_FAT | GO:0050804~regulation of synaptic transmission |
| GOTERM_BP_FAT | GO:0051971~positive regulation of transmission of nerve impulse |
| Annotation Cluster 23 | Enrichment Score: 1.3601123868654303 |
| Category | Term |
| KEGG_PATHWAY | hsa04350:TGF-beta signaling pathway |
| GOTERM_BP_FAT | GO:0030509~BMP signaling pathway |
| GOTERM_BP_FAT | GO:0007178~transmembrane receptor protein serine/threonine kinase signaling pathway |
| Annotation Cluster 24 | Enrichment Score: 1.357474283813374 |
| Category | Term |
| GOTERM_BP_FAT | GO:0001501~skeletal system development |
| GOTERM_BP_FAT | GO:0001503~ossification |
| GOTERM_BP_FAT | GO:0060348~bone development |
| GOTERM_BP_FAT | GO:0001649~osteoblast differentiation |

Example 2

Figure 4:
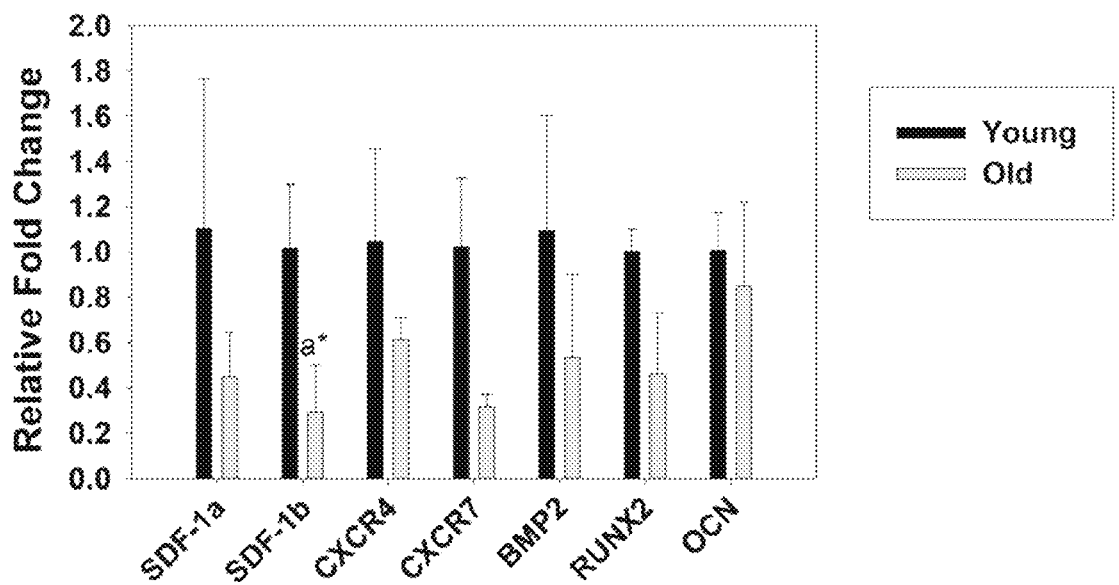
FIG. 4 is a bar graph showing relative fold change of various miRNA isolated from old and young CD271+human BMSCs as determined by qRT-PCR. Statistically significant differences are identified between Young vs Old CD271+ BMSCs, a*P<0.05.

Osteogenic mRNA Levels Reduce with Age qRT-PCR on mRNA isolated from CD271+BMSCs was performed. As shown in FIG. 4, both the isoforms of SDF-1 along with osteogenic genes such as BMP2 and RUNX2 were reduced with age. Statistically significant differences are identified between Young vs Old CD271+BMSCs, a*P<0.05.

Example 3

Figures 5A, 5B, 5C, 5D:
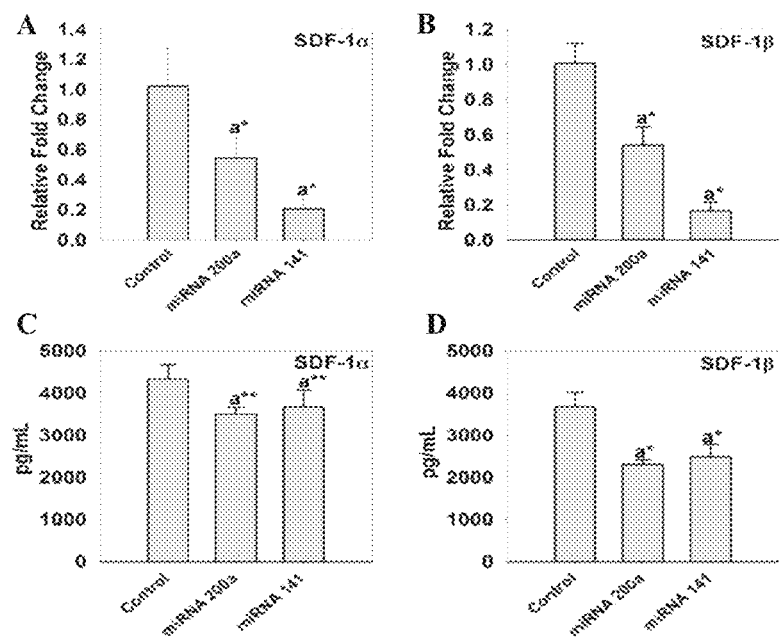
FIGS. 5A and 5B are bar graphs showing the relative fold change of SDF-1alpha (FIG. 5A) and SDF-1beta (FIG. 5B) in control cells, and cells transfected with SDF-1-targeting miR-NAs miR-200a or 141 as determined by qRT-PCR. Control and other groups (*p<0.001, **p<0.05).
FIGS. 5C and 5D are bar graphs showing the pg/mL of SDF-1alpha (FIG. 5C) and SDF-1beta (FIG. 5D) protein expressed and secreted from control cells, and cells transfected with SDF-1-targeting miR-NAs miR-200a or 141 as determined by ELISA. Control and other groups (*p<0.001, **p<0.05).
Figure 6:
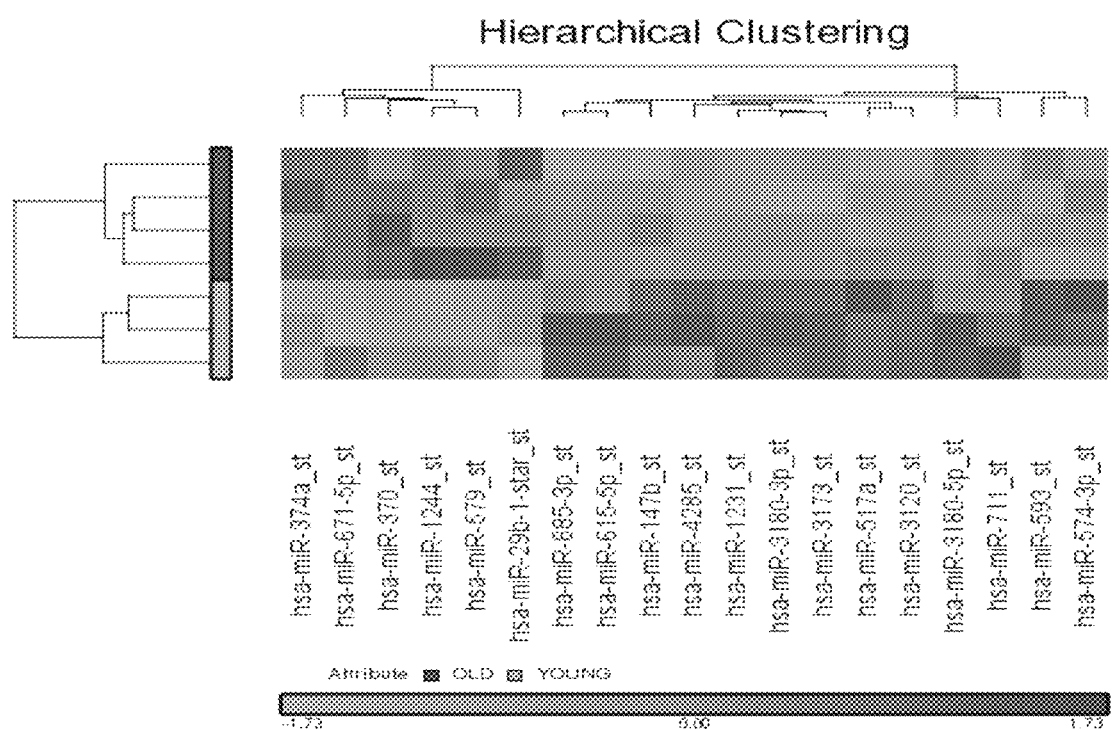
FIG. 6 is a heat map showing hierarchical clustering analysis of levels of miRNA in CD271 + human BMSCs. The heat map illustrates miRNAs that either went up or down consistently with age.

Transfection with SDF-1-Targeting miRNAs Reduce SDF-1α & β mRNA and Protein Expression in Murine BMSCs FIGS. 5A and 5B show that SDF-1α & β mRNA level decrease with miR-200a & 141 predicted to target SDF-1.

FIGS. 5C and 5D show the results of ELISA analysis of SDF-1α & β protein expression and secretion into culture media. Statistically significant differences are identified between Control and other groups (*p<0.001, **p<0.05)

Collectively, Examples 1, 2, and 3 show that the differential miRNA expression in human BMSCs with age can regulate age-associated changes that reduce osteogenic capacity and increase the adipogenic fate of these stem cells, and may help drive the development of osteoporosis. Targeting these miRNAs may be a potential therapeutic strategy to treat age-related musculoskeletal disorders.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of increasing the osteogenic potential of cells in a subject in need thereof comprising administering to a subject in need thereof a composition comprising an effective amount of an agent that reduces the levels of hsa-miR-29b-1*, wherein the agent is a functional nucleic acid that targets hsa-miR-29b-1*.

2. The method of claim 1 wherein the functional nucleic acid is an antagomir, wherein the antagomir hybridizes with hsa-miR-29b-1*.

3. The method of claim 1 wherein the agent increases expression or bioavailability of a protein selected from the group consisting of SDF-1, BMP2, β arrestin, SOX4, Leptin, IGF-1, VEGF, Collagen type 1 α1 and Collagen type 1 α2.

4. The method of claim 1 wherein the subject exhibits symptoms of shoulder, elbow, hip, neck, or foot pain, osteoarthritis, osteoporosis, fibromyalgia, and reduced strength.

5. The method of claim 4 wherein the subject is at least 64 years old.

6. A method of increasing the osteogenic potential of cells in a subject in need thereof comprising
   treating isolated human bone marrow mesenchymal stromal cells ex vivo with a composition comprising an agent that reduces the levels of hsa-miR-29b-1* in an effective amount to increase expression of SDF-1, BMP2, βarrestin, SOX4, Leptin, IGF-1, VEGF, Collagen type 1α1 or Collagen type 1α2 in the cells; and
   administering the treated cells to a subject in need thereof in an effective amount to increase the osteogenic potential of the cells.

7. The method of claim 6 wherein the isolated cells are reprogrammed ex vivo to alter the miRNA expression profile of the cells to be more similar to the miRNA expression profile of cells isolated from subjects from 29-41 years of age than untreated cells.

8. The method of claim 6 wherein the agent is a functional nucleic acid that targets hsa-miR-29b-1*.

9. The method of claim 8 wherein the functional nucleic acid is an antagomir.

10. The method of claim 6 wherein the subject exhibits symptoms of shoulder, elbow, hip, neck, or foot pain, osteoarthritis, osteoporosis, fibromyalgia, and reduced strength.

11. The method of claim 6 wherein the subject is at least 64 years old.

12. The method of claim 1, wherein the agent is administered to the subject in an amount effective to increase the osteogenic capacity of bone marrow stromal cells (BMSC) in the subject.

13. The method of claim 2, wherein the antagomir is delivered in an injectable hydrogel formulation.

14. The method of claim 2, wherein the antagomir is delivered in a nanoparticle formulation.

15. The method of claim 13, further comprising targeted systemic delivery of the formulation, wherein the formulation is targeted to the diseased tissue.

16. The method of claims 13, further comprising local delivery of the formulation to the diseased tissue.

17. The method of claim 15, wherein the targeted systemic delivery is achieved by intravenous infusion.

* * * * *